United States Patent [19]
Schmitz

[11] Patent Number: 5,795,350
[45] Date of Patent: Aug. 18, 1998

[54] DISPOSABLE ABSORBENT ARTICLE HAVING A MECHANICAL FASTENER

[75] Inventor: Christoph Johann Schmitz, Euskirchen-Stotzheim, Germany

[73] Assignee: The Procter & Gamble Company, Cincinnati, Ohio

[21] Appl. No.: 860,123

[22] PCT Filed: Dec. 13, 1995

[86] PCT No.: PCT/US95/16669
§ 371 Date: Jun. 30, 1997
§ 102(e) Date: Jun. 30, 1997

[87] PCT Pub. No.: WO96/20676
PCT Pub. Date: Jul. 11, 1996

[30] Foreign Application Priority Data
Dec. 29, 1994 [EP] European Pat. Off. ............. 94120878

[51] Int. Cl.[6] .................................................. A61F 13/15
[52] U.S. Cl. .......................... 604/391; 604/389; 604/390
[58] Field of Search ............................. 604/358, 370, 604/385.1, 385.2, 386, 387, 389, 390, 391

[56] References Cited

U.S. PATENT DOCUMENTS

| | | | |
|---|---|---|---|
| 4,014,340 | 3/1977 | Cheslow | 128/287 |
| 4,585,450 | 4/1986 | Rosch et al. | 604/390 |
| 4,869,724 | 9/1989 | Scripps | 604/389 |
| 5,057,097 | 10/1991 | Gesp | 604/389 |

*Primary Examiner*—Mickey Yu
*Assistant Examiner*—Francis K. Cuddihy
*Attorney, Agent, or Firm*—David M. Weirich; Steven W. Miller; Jacobus C. Rasser

[57] ABSTRACT

An absorbent article is comprised of two hook-type fastening members and a loop member for mechanically engaging with the hook-type members. The easily manufactured landing member, a section of the backsheet, is of low bulk and can be elastically contracted and extended.

8 Claims, 4 Drawing Sheets

DISPOSABLE ABSORBENT ARTICLE HAVING A MECHANICAL FASTENER

FIELD OF THE INVENTION

The invention relates to disposable absorbent articles comprising a mechanical fastening system.

Such a disposable absorbent articles are known from EP-A- 0 321 234.

Known mechanical fastening systems for use in disposable absorbent articles comprise tape tabs in the back waist region having hook-type fastening elements, which mechanically engage with a landing member in the front waist region. The landing member is a patch or strip of a loop-type material which is attached to the backsheet. The loop type material entangles with the hooks and has resistance against peel forces and shear forces.

The loop-type material used in the landing zone of the known mechanical fastening system is formed by a separate patch of material, attached to the garment-facing side of the backsheet. Such loop-type materials are a relatively expensive materials.

Furthermore, as the known loop- type materials are attached to the garment-facing side of the backsheet, the bulk of the absorbent articles is increased when these are packed in a compressed array.

Another drawback of the addition of separate patches of loop-type material in the landing zone is an increase in the complexity of the production process for making an absorbent article.

Furthermore, it is difficult to attach larger patches of loop-type material when the front waist region is made of an elasticated or of an elastically extensible material, such that the backsheet material is garthered. The patches of loop-type material, which are non-extendible and non-elastic, may impair the elastic properties of the front waist region.

It is therefore an object of the present invention to provide an absorbent article having a mechanical fastening system which is of simple construction and which is cost-effective.

It is another object of the invention to provide an absorbent article comprising a mechanical fastening system which is of low bulk when packed in a compressed array.

It is another object of the invention to provide an absorbent article comprising a mechanical fastening system which can effectively be combined with an elasticated waist region without impairing the elasticity thereof.

SUMMARY OF THE INVENTION

An absorbent article according to the invention comprises a garment-facing backsheet having two longitudinal sides, a front transverse edge, and a back transverse edge. The article has a mechanical closing system comprising at least two hook-type fastening members located in the region of the back transverse edge and extentending transversely beyond each longitudinal side. A landing member is located in the region of the front transverse edge for mechanically engaging with the hook-type fastening member. The backsheet comprises a first section having a front peripheral edge which is located outside the landing zone, and a second section joined to the first section. The second section of the backsheet comprises a different material than the first section and is at least partly located in the front waist region so that the second section forms the landing member.

The first section of the backsheet underlies the absorbent core and may be formed by a liquid-impervious thermoplastic film or a film/fabric colaminate, the second section comprising a non-woven or other loop-type material which is adapted to engage with the hook-type material of the fastening members. In this way a soft and compliant waist panel is obtained in the front waist region to which no separate patches of looptype material need be attached. Hence a process simplification is obtained, and no additional bulk is added to the backsheet.

Furthermore, since the landing member is formed by the front waist section of the backsheet, the landing member substantially completely extends along the full width of the front transverse edge of the backsheet, and hence allows for numerous positions of attachment of the hook-type fastening members.

In case the front waist region is elasticated and is contracted in gathers by an elastic element, the landing member does not interfere with the elastic properties of the front waist region.

Furthermore, the front waist region of the absorbent article according to the invention may comprise surface irregularities to which separate patches of conventional loop-type material can only be attached with difficulty. Such surface irregularities may be provided by mechanical pre-straining of the front waist region between two intermeshing corrugated rolls to impart extensibility to the front waist region. Such a process is described in U.S. Pat. No. 5,196,000 and U.S. Pat. No. 5,236,430.

For backsheet materials forming the landing zone, which materials may be nonwoven materials, that have relatively little surface irregularities, relatively small and sharply pointed hooks will be required for the hook-type material. For backsheet materials in the landing zone which comprise a relatively larger number of loops projecting outwardly form the backsheet surface, the hooks of the hook-type material may be of larger size and may be relatively flexible. Alternatively, the surface texture of the second section of the backsheet can be selected to match a given type of hook-fastening material to achieve proper fastening. In one embodiment of the article according to the invention, the front waist section of the backsheet is subjected to mechanical deformation to impart increased surface texture to that layer for improved attachement of the hooks thereto. Such mechanical deformation may be imparted by passing the inner layer between two corrugated intermeshing rolls, as mentioned above.

By using in the landing zone a nonwoven material which also forms a waist panel of the backsheet, no additional loop-type material need be employed as a landing member. This results in reduced costs of the absorbent article according to the invention.

The second section of the backsheet may be an elastic non-woven material or may comprise an elastic member attached to a non-elastic fibrous layer, such as an elastomeric film attached to the user-facing side of the second section of the backsheet along the front waist edge. The use of an elastic member on second section of the backsheet not only maintains a snug fit of the article around the waist of the wearer, but has as an additional advantage that the material of the second section of the backsheet is contracted to form gathers, which provide improved attachement with the hook-type material of the hook-type landing members. Preferably the material of the second section is previous to vapor such that ventilation of the skin located below the backsheet in the front waist region takes place.

The backsheet section located outside the landing zone may be comprised of a non-woven material, a thermoplastic film or a laminate of a non-woven material and a film. This backsheet section may be formed of elastomeric material. There may be additional layers located between the topsheet and the backsheet which are of equal length as the backsheet and do not project beyond the backsheet's front transverse edge.

BRIEF DESCRIPTION OF THE DRAWINGS

The invention will be described with reference to the accompanying drawings. In the drawings.

DETAILED DESCRIPTION OF THE INVENTION

Mechanical closing systems of the present invention are useful and beneficial when applied to disposable absorbent articles. As used herein, the term "disposable absorbent article" refers to articles which absorb and contain body exudates and, more specifically, refers to articles which are placed against or in proximity to the body of the wearer to absorb and contain the various exudates discharged from the body and which are intended to be discarded after a single use (i.e., they are not intended to be laundered or otherwise restored or reused). A preferred embodiment of the disposable absorbent article of the present invention is a diaper 20. As used herein, the term "diaper" refers to a garment generally worn by infants or incontinent persons that is drawn up between the legs and fastened about the waist of the wearer. Examples of the kinds of diapers to which the present invention is very readily adapted are shown in the above-referenced U.S. Pat. Re. 26,1 51 issued to Duncan et al. and in U.S. Pat. 3,860,003 entitled "Contractable Side Portions for Disposable Diaper" which issued to Kenneth B. Buell on Jan. 14, 1975.

It will be apparent form the following description that the mechanical fastening system illustrated and described herein may be applied to the body portion of such diapers. On the other hand, it will be understood that the invention is not limited to any specific diaper structure or configuration.

Figure 1:
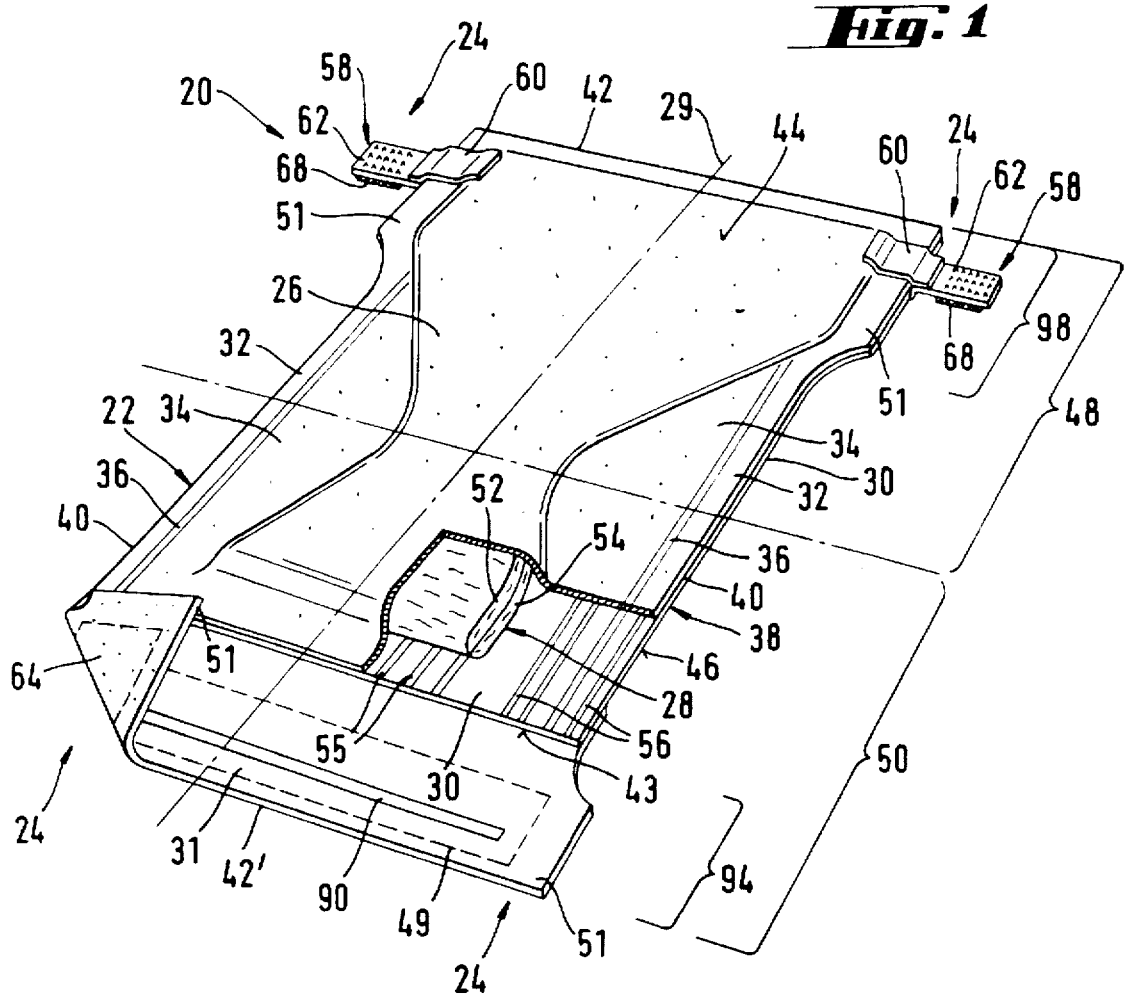
FIG. 1 shows a partially cut-away perspective view of a disposable diaper having a landing member according to the invention.

Referring to the drawings, it will be noted that FIG. 1 is a partially cut-away perspective view of the diaper 20 of the present invention prior to its being placed on the diaper wearer by the diaper user. As can be seen in FIG. 1, a preferred diaper 20 comprises a body portion 22 and a fastening system 24. A preferred body portion 22 comprises a liquid previous topsheet 26, an absorbent core 28, a liquid impervious first backsheet section 30, a second backsheet section 31, and elastically contractible leg cuffs 32 comprising a side flap 34 and one or more elastic members 36. The first section 30 and the second section 31 of the backsheet are mutually connected in the proximity of a front peripheral edge 43 of the first section 30. The second section 31 of the backsheet defines a landing zone 49 for attaching to the mechanical fastening members 58. While the topsheet 26, the absorbent core 28, the backsheet sections 30,31, the side flaps 34, and the elastic members 36 may be assembled in a variety of well-known configurations, a preferred disposable diaper configuration is shown and described generally in the above-referenced U.S. Pat. No. 3,860,003 which issued to Kenneth B. Buell on Jan. 14, 1975.

FIG. 1 shows a preferred embodiment of the body portion 22 in which the topsheet 26 and the backsheet section 30 are coextensive and have length and width dimensions generally larger than those of the absorbent core 28. In FIG. 1, the topsheet 26 is superposed on the backsheet section 30 but may alternatively cover both backsheet sections 30,31 thereby forming the periphery 38 of the body portion 22. The periphery 38 defines the outer perimeter or, in other words, the outer extend of the body portion 22. The periphery 38 comprises longitudinal sides 40 and end edges or transverse edges 42, 42'. The body portion 22 has user-facing side 44 and garment-facing 46. In general, the garment-facing side 46 of the diaper 20 extends from back transverse edge 42 to front transverse edge 42' of the diaper and from one longitudinal side 40 to the other longitudinal side 40 of the diaper and is the surface farthest from the wearer during use of the diaper 20. The garment-facing side of any layer comprised in the diaper 20 is the side of the layer farthest from the wearer during use. The user-facing side 44 is that surface of the diaper opposite the garment-facing side 46 and in the embodiment shown is typically formed by the topsheet 26. In general, the user-facing side 44 of the diaper 20 is that surface coextensive with the garment-facing side 46 and which is for the greater part in contact with the wearer when the diaper 20 is worn. The user-facing side of any layer comprised in the diaper 20 is that side of layer which is closest to the wearer during use.

The diaper 20 has first and second end regions 48 and 50, respectively, extending from the transverse edges 42, 42' of the diaper periphery 38 towards the transverse centerline of the diaper 20. Both the first end region 48 and the second end region 50 extend a distance of about one-half of the length of the diaper 20 such that the end regions comprise each half of the diaper 20.

Both the first end region 48 and the second end region 50 have panels 51. The panels 51 are those portions of the first end region 48 and the second end region 50 which overlap when the diaper 20 is fastened about the waist of the wearer.

The extent to which the end regions overlap and thus the extent to which the panels 51 are formed will depend on the overall dimensions and shape of the diaper 20 and the size of the wearer.

The absorbent core 28 of the body portion 22 may be any means which is generally compressible, conformable, non-irritating to the wearer's skin, and capable of absorbing and retaining liquids and certain body exudates. The absorbent core 28 may be manufactured in a wide variety of sizes and shapes (e.g., rectangular, hourglass, asymmetric, etc.) and from a wide variety of liquid absorbent materials commonly used in diapers and other disposable absorbent articles, such as comminuted wood pulp which is generally referred to as the airfelt. Examples of other suitable absorbent materials include creped cellulose wadding, absorbent foams, absorbent sponges, superabsorbent polymers, absorbent gelling materials, or any equivalent materials or combination of materials. The total absorbent capacity of the absorbent core 28 should, however, be compatible with the design exudate loading in the intended use of the diaper 20. Further, the size and absorbent capacity of the absorbent core 28 may varied to accommodate wearers ranging from infants to adults.

While the absorbent core 28 may comprise a single layer of absorbent material such as the configuration described in U.S. Pat. No. 4,610,678 entitled "High-Density Absorbent Structure" which issued to Paul T. Weisman and Steven A. Goldman on Sep. 9, 1986 a preferred embodiment of the absorbent core 28 is a dual-layered absorbent core in a preferred configuration such as is generally described in U.S. Pat. No. 4,673,402 entitled "Absorbent Article With Dual-Layered Cores" which issued to Paul T. Weisman, Dawn I. Houghton and Dale A. Gellert on Jun. 16, 1987, having an asymmetric-shaped upper layer 52 and a lower layer 54. The upper layer 52 preferably acts as a liquid acquisition/distribution layer comprised primarily of hydrophilic fiber material. The lower layer 54 acts as a liquid storage layer comprised of a mixture of hydrophilic fiber material and particles of an absorbent gelling material (hydrogel material).

Both the upper layer 52 and the lower layer 54 preferably comprise an absorbent layer encased in a tissue layer. It should be understood, however, that the size, shape, configuration, and total absorbent capacity of the upper layer 52 or the lower layer 54 may be varied to accommodate wearer's ranging from infants through adults. Therefore, the dimensions, shape, and configuration of both the upper layer 52 and the lower layer 54 may be varied (e.g., the upper layer or the lower layer may have a varying caliper, a hydrophilic gradient, a rapid acquisition zone or may contain absorbent gelling material).

The absorbent core 28 is superposed on the first and second backsheet sections 30,31 and is preferably associated thereto by a core attachment means 55 such as those well known in the art, for example, pressure-sensitive adhesives, hot melt adhesives or other adhesives; ultrasonic bonding; or heat/pressure sealing. The absorbent core 28 may be secured to the backsheet section 30,31 by a uniform continuous layer of adhesive, a patterned layer of adhesive, or any array of separate lines or spots of adhesive. And adhesive which has been found to be satisfactory is preferably a hot-melt adhesive such as manufactured by Eastman Chemical Products Company of Kingsport, Tennessee and marketed under the tradename of Eastobond A-3 or by Century Adhesives, Inc., of Columbus, Ohio and marketed under the tradename Century 5227. The core attachment means 55 preferably comprise an open pattern network of filaments of adhesive as is shown in U.S. Pat. No. 4,573,986 entitled "Disposable Waste-Containment Garment" which issued to James A. Minetola and David R. Tucker on Mar. 4, 1986.

The first backsheet section 30 is impervious to liquids and is preferably manufactured from a thin plastic film, although other flexible liquid impervious materials may also be used. The first backsheet section 30 prevents the exudates, absorbed and contained in the absorbent core 28 from soiling articles which contact the diaper 20 such as bedsheets and undergarments. Preferably, the backsheet section 30 is a polyethylene film having a thickness of from 0.012 mm (0.5 mil) to 0.051 mm (2.0 mils), although other flexible, liquid impervious materials may be used. As used herein, the term "flexible" refers to materials which are compliant and which will readily conform to the general shape and contours of the human body.

A suitable polyethylene film is manufactured by Monsanto Chemical Corporation and marketed in the trade as Film No. 8020. The backsheet section 30 is preferably embossed and/or matte finished to provide a more clothlike appearance. Further, the backsheet section 30 may permit vapors to escape from the absorbent core 28 while still preventing exudates from passing through the backsheet section 30.

The second backsheet section 31 need not be liquid-impervious and is preferably formed by a non-woven material which is suitable to engage with the mechanical fastening members 58. The second section 31 may for instance be formed form the same material as the topsheet 26. The second section 31 is connected to the first section 30 to form an integral backsheet.

The size of the integral backsheet 30,31 is dictated by the size of the absorbent core 28 and the exact diaper design selected. In a preferred embodiment, the integral backsheet 30,31 has a modified hourglass shape extending beyond the absorbent core a minimum distance of at least 0.5 to 8 cm, preferably of 1.3 cm to 2.5 cm around the entire diaper periphery 38.

The topsheet 26 of the body portion 22 of the present invention is compliant, soft feeling, and non-irritating to the wearer's skin. Further, the topsheet 26 is liquid previous permitting liquids to readily penetrate through its thickness. A suitable topsheet 26 may be manufactured from a wide range of materials such as porous foams, reticulated foams, apertured films, natural fibers (e.g. wood or cotton fibers), synthetic fibers (e.g., polyester or polypropylene fibers) or from a combination of natural and synthetic fibers. Preferably, it is made of a hydrophobic material to isolate the wearer's skin from liquids retained in the absorbent core 28.

A particularly preferred topsheet 26 comprises staple length polypropylene fibers having a denier of about 1.5, such as Hercules Type 151 polypropylene fibers marketed by Hercules, Inc. of Wilmington, Del. As used herein, the term "staple length fibers" refer to those fibers, having a length of at least 15.9 mm (0.625 inches).

There are a number of manufacturing techniques which may be used to manufacture the topsheet 26. For example, the topsheet 26 may be woven, nonwoven, spunbonded, carded, hydroformed or the like. A preferred topsheet 26 is carded and thermally bonded by means well-known to those skilled in the fabric art. Preferably, the topsheet 26 has a basis weight from 15 to about 30 grams per square meter, a minimum dry tensile strength of at least 400 grams per centimeter in the machine direction and a wet tensile strength of at least 55 grams per centimeter in the cross-machine direction.

The topsheet 26 and the first backsheet section 30 are associated together in any suitable manner as is well known in the diaper manufacturing art. As used herein, the term "associated" encompasses configurations whereby the topsheet 26 is directly joined to the integral backsheet 30,31 by affixing the topsheet 26 directly to at least one of the backsheet sections 30,31 and configurations whereby the topsheet 26 is indirectly joined to the backsheet sections 30,31 by affixing the topsheet 26 to intermediate members which in turn are affixed to the backsheet sections 30,31. In a preferred embodiment, the topsheet 26 and the backsheet sections 30,31 are joined directly to each other in the diaper periphery 38 by a flap attachment means 56 such as an adhesive or any other attachment means as is known in the art. In general, the core attachment means 55 that affixes the absorbent core 28 to the backsheet sections 30,31 is the same means as the flap attachment means 56 that affixes the topsheet 26 to the backsheet sections 30,31. Thus, for example, a uniform continuous layer of adhesive, a patterned layer of adhesive, an array of separate lines or spots of adhesive, or a network of adhesive filaments such as shown in the above-referenced U.S. Pat. No. 4,573,986 may be used.

Elastically contractible leg cuffs 32 are disposed adjacent the periphery 38 of the body portion 22, preferably along each longitudinal edge 40, so that the leg cuffs 32 tend to draw and hold the diaper 20 against the legs of the wearer. While the leg cuffs 32 may comprise any of several means as are well known in the diaper art, a particularly preferred leg cuff construction comprises a side flap 34 and one or more elastic members 36, as is described in detail in the hereinbefore referenced U.S. Pat. No. 3,860,003. In addition, a method and apparatus suitable for manufacturing a disposable diaper having elastically contractible leg cuffs are described in U.S. Pat. No. 4,081,301 entitled "Method and Apparatus For Continuously Attaching Discrete, Stretched Elastic Strands to Predetermined Isolated Portions of Disposable Absorbent Articles" which issued to Kenneth B. Buell on Mar. 28, 1978.

In a preferred embodiment, the elastically contractible leg cuff 32 comprises a side flap 34 and an elastic member 36 comprising an elastic thread.

The diaper 20 is provided with a fastening system 24 for forming a side closure. Thus, the diaper 20 is fitted to the wearer and the first end region 48 and the second end region 50 are maintained in an overlapping configuration when the diaper 20 is worn.

In a preferred embodiment of the present invention as show in FIG. 1, the fastening system 24 comprises fastening members 58, preferably comprising a tape tab 60 and a hook-type fastening element 62, disposed adjacent each longitudinal side 40 of the body portion 22 in the back waist region 98 of the first end region 48; a landing member 64, engageable with the hook-type fastening element 62, disposed on the outside surface 46 of the body portion 22 in the front waist region 94. The landing member 64 is comprised of the second backsheet section 31 which is located in the landing zone 49. In FIG. 1, the landing zone 49 has been indicated with a dashed line. Additional fastening/disposal means 68 may be positioned on the tape tab 60, for allowing the diaper 20 to be secured in a disposal configuration so as to provide convenient disposal of the diaper 20.

Each fastening member 58 is intended to provide a mechanical fastening means for engaging the landing member 64 so as to provide a secure side closure for the diaper 20.

The fastening member 58 comprises combination of a hook-type fastening element and adhesive attachment means positioned on the body portion 22 of the diaper 20. The hook-type fastening element 62 of each fastening member 58 is joined to the body portion and preferably covers an area 25 mm wide (i.e., generally perpendicular to the longitudinal centerline 29) by 62.5 mm long (i.e., generally parallel to the longitudinal centerline 29) at the panels 51 of the body portion 22. An exemplary embodiment of a hook-type fastening member 62 is described in U.S. Pat. No. 4,699,622 entitled "Disposable Diaper Having an Improved Side Closure" issued to John W. Toussant and Margaret H. Hasse on Oct. 13, 1987.

Figure 2:
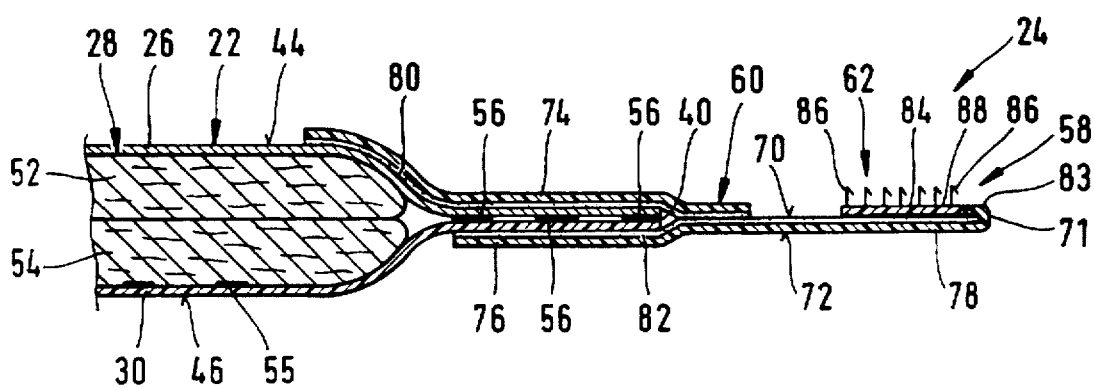
FIG. 2 shows a cross-sectional view through a hook-type fastening member 58 of FIG. 1 along a line of cross-section parallel to the back transverse edge.

As shown in FIGS. 1 and 2, the fastening member 58 most preferably comprises a tape tab 60. Any of the well known configurations and constructions of a tape tab may be used.

A preferred tape tab 60 is a Y-shaped tape tab as described in detail in GB-A-1458566. Alternatively preferred tape tabs are described in detail in co-pending European Pat. Application No. 87300450.1.

A particularly preferred tape tab 60 is illustrated in FIG. 2 and has a fastening surface 70 and a backing surface 72. The fastening surface 70 is that surface of the tape tab 60 designed to engage the landing member 64 of the present invention. Thus, the fastening surface 70 of the tape tab 60 will generally correspond to the garment-facing side 44 of the body portion 22. The backing surface 72 is that surface opposite of the fastening surface 70 and generally corresponds to the outside surface 46 of the body portion 22. The backing surface 72 is thus generally exposed during wear of the diaper 20.

The preferred tape tab 60 illustrated in FIG. 2 is one which is anchored to both the user-facing side 44 and the garment-facing side 46 of the body portion 22 to create a manufacturer's end (i.e., that attachment of the tape tab 60 to the diaper 20 made during manufacture of the diaper 20). The tape tab 60 has another element which forms the user's end i.e., that joint made by the person in securing the diaper to the wearer). Thus, the preferred tape tab 60 of the present invention has at least three elements, a first fixed portion 74, a second fixed portion 76, and a connective portion 78. The first fixed portion 74 is that portion of the tape tab 60 which is attached to the user-facing side 44 of the body portion 22. The second fixed portion 76 is that portion of the tape tab 60 which is attached to the garmentfacing side 46 of the body portion 22. The first fixed portion 74 and the second fixed portion 76 thus form the manufacturer's end of the tape tab 60. The connective portion 78 is that portion of the tape tab 60 which is attached to another portion of the diaper 20, generally the landing member 64 by the user when securing the diaper 20 on the wearer. The connective portion 78 thus forms the user's end. Additionally, the outer surface of the second fixed portion 76 and the outer surface of the connective portion 78 form the backing surface 72 of the tape tab 60 while the inner surface of the first fixed portion 74 and the inner surface of the connective portion 78 form the fastening surface 70 of the tape tab 60.

The preferred Y-shaped tape tab 60 of the present invention can be constructed in several ways. The first fixed portion 74, the second fixed portion 76, and the connective portion 78 can each be separate tapes which meet and are joined adjacent the longitudinal edge 40 of the body portion 22 in an area of joinder. A more practical structure for the tape tab 60 is one in which the connective portion 78 and either the first fixed portion 74 or the second fixed portion 76 are a unitary strip of tape material. If the connective portion 78 is unitary with the second fixed portion 76 as shown in FIG. 2, then the first fixed portion 74 is a separate element which is attached to the combined connective portion and the second fixed portion adjacent to the longitudinal side 40 of the body portion 22.

FIG. 2 also shows tab attachment means for securing the tape tab 60 to the body portion 22. These tab attachment means are any of those attachment means which provide an adequate bond, and preferably are any of the pressure-sensitive adhesives well-known to those of ordinary skill in the adhesive art. The outer surface of the first fixed portion 74 is affixed to the user-facing side 44 of the body portion 22 by a first tab attachment means 80. The inner surface of the second fixed portion 76 is affixed to the garment-facing side 46 of the body portion 22 by a second tab attachment means 82. The connective portion is provided with a hook-type fastening element 62 joined to it preferably by the second tab attachment means 82 (alternatively, a third tab attachment means if the connective portion 78 is a separate element from the second fixed portion 76), although a separate adhesive attachment means may be placed on the hook-type fastening element 62 separately and the combined material joined to the connective portion 78.

Preferred materials for the tape tabs 60 comprises a tape material such as tape code numbers XPF 14.43.0, Y-9376, or Y-9030 available from The Minnesota Mining and Manufacturing Company, St. Paul, Minn. The tape material in the embodiments are preferably a polyethylene film having a tab attachment means tailored to bond to the polyethylene positioned on the tape material. The tape tab attachment means may comprise any of those adhesives which provide an adequate bond with other portions of the diaper, and is preferably any of the pressure sensitive adhesives well-known to those of ordinary skill in the art. Preferred tab attachment means is a pressure-sensitive adhesive such as code number XPF 1.42.34 available from The Minnesota Mining an Manufacturing Company, St. Paul, Minn.

As shown in FIG. 2, the tape tab 60 may also have a grip tab 83 at the distal edge 71 in the connective portion 78. The grip tab 83 may be formed by folding over a small margin of the distal edge 71 of the connective portion 78 and attaching it to itself. This forms an end on the connective portion 78 which is easier to grasp by the diaper user when the diaper 20 is to be fitted and attached to the wearer. The grip tab 83 is most beneficial when used when the connective portion 78 is superposed on the first fixed portion 74.

The hook-type fastening element 62 of the present invention comprises a hook fastening material 84. As used herein, the term "hook fastening material" is used to designate a material having engaging elements 86. It should also be understood that the use of the term "hook" should be non-limiting in the sense that the engaging elements 86 may comprise any shapes as are known in the art so long as they are adapted to engage a complementary second fastening element. As shown, the hook fastening material 84 preferably comprises a base 88 having a first surface and a second surface and a plurality of engaging elements 86 extending from the first surface of the base 88. Each of the engaging elements 86 are shown to comprise a stem supported at one end on the first surface of the base and an enlarged head positioned at the end of the stem opposite of the base.

The hook-type fastening material 84 of the present invention is intended to engage fibrous elements of fibrous material in the landing zone 49 on the user-facing side 44 of the backsheet. Thus, the hook-type fastening material 84 may be manufactured from a wide range of materials. Suitable materials include, nylon, polyester, polypropylene, or any combination of these materials. A suitable hook fastening material 84 comprises a number of shaped engaging elements 86 projecting from a woven backing such as the commercially available material designated "Scotchmate" brand No. FJ3402 available from Minnesota Mining and Manufacturing Company, St. Paul, Minn. Alternatively, the engaging elements may have any shape such as hooks, "T's" or any other shape as are well known in the art. A particularly preferred hook fastening material is described in C. Locke Scripps' co-pending U.S. patent application Ser. No. 07/007,841 entitled "Disposable Diaper Having An Improved Fastening Device" filed Jan. 26, 1987.

Other suitable hook-type materials for use in the present invention are for instance extruded hooks available under the reference MC5 from the Minnesota Mining and Manufacturing Company, ST. Paul, Minn. or printed hooks available from the same company under references CS200 and MC6. Other suitable hook-type materials are available under reference 942 or 960E from Aplix, Inc., P.O. Box 7505, Charlotte, N.C. 28241.

The loop-type material of the landing member 64 is adapted to engage with the hook-type fastening element 62.

As used herein, the term "loop-type" material is intended to mean any fibrous material which can mechanically engage with the hook-type material of the fastening members 58 to maintain the diaper 20 affixed around the waist of a wearer.

Other suitable loop-type materials for use in the present invention may comprise woven materials such as brushed loops available from Texmaille S.A., Rue Pasteur, 02610 Moy de L'aisne, France; double knit loops available from Tissages de Quintenas S.A., Parc d'activités de marenton, B.P.158-07104 Annonay, France; and Linerless loops available under reference LLL from the Minnesota Mining and Manufacturing Company.

Again other suitable loop-type materials are formed by non-woven materials.

In general, the materials of the hook-type fastening members 58 and the loop-type landing member 64 should be selected such that the peel force of a 30 mm wide patch of hook-type material is between 3 and 20N, preferably about 7–8N and the shear force of a patch of hook-type material of dimensions of 30×13 mm is between 10 and 100N, preferably about 50N.

The tests for measuring the peel forces and the shear forces exerted by the hooktype fastening members 58 on the loop type landing member 64 are described below.

I. 135°-Peelforce Test

This method describes the procedure for measuring the peel force, in grams, of the combined hook-type fastening member and loop-type landing member. The materials under test are mounted on a steel plate-sled assembly and are separated at a constant peel angle of 135°.

During the test the temperature is maintained at 73°±2° F. The relative humidity is controlled at 50±2%.

A patch of loop-type material measuring 2 in.×4 in. is placed on a 2 in.×8 in.×0.06 in. steel plate with a double-sided tape of the same dimensions as the patch of loop-type material.

A patch of hook-type material measuring 1 in.×0.75 in. is attached to a tape tab of similar kind as the tape tab 60 shown in FIG. 1, adjacent the area of the grip tab 83, further referred to in this test method as the leading edge of the tape tab 60. No actual grip tab needs be present at the leading edge of the tape tab 60 during testing. If the hooks of the hook-type material are angled with respect to the tape tab, the hooks are oriented to be inclined towards the leading edge.

The hook-type material is placed on the loop- type landing member. Subsequently, a rubber-coated steel roller of diameter of 3.25 in., a width of 1.75 in. and a weight of 4.5 lbs is rolled back and forth in the length direction of the tape tab 60 twice (a total of four passes).

The steel plate with the attached hook-type and loop-type materials is mounted into an INSTRON test apparatus, Model 4201, which is set to have a cross-head speed of 12 in./minute and a Load Cell of 1 kg.

The steel plate is slidably mounted in a sled which is carried by the lower jaw of the INSTRON apparatus.

The leading edge of the tape tab 60 is placed in the upper jaw of the INSTRON apparatus.

The upper cross head is set in motion to pull the leading edge of the tape tab 60 off the loop-type landing member at an angle of 135° with respect to the loop-type landing member. The steel test plate on which the loop-type landing member is mounted, is moved in the sled consecutively with the cross head relative to the lower jaw to maintain a constant angle of 135° during the full cycle of peeling off the tape tab.

The peak force, in grams, is recorded for at least four samples and is averaged.

II. 180° Shear Test

This method describes the procedure for measuring the shear force, in grams, of the combined hook-type fastening member and loop-type landing member. The materials under test are mounted on a steel plate and are separated at a constant peel-angle of 180°.

During the test the temperature is maintained at 73°±2° F. The relative humidity is controlled at 50±2%.

A patch of loop-type material measuring 2 in.×5 in. is placed on a 2 in.×5 in.×0.06 in. steel plate with a double-sided tape of the same dimensions as the patch of loop-type material.

A patch of hook-type material measuring 1 in.×0.75 in. is attached to a tape tab of similar kind as the tape tab 60 shown in FIG. 1, adjacent the area of the grip tab 83, further referred to in this test method as the leading edge of the tape tab 60. No actual grip tab needs be present at the leading edge of the tape tab 60 during testing. If the hooks of the hook-type material are angled with respect to the tape tab, the hooks are oriented to be inclined away from the leading edge.

The hook-type material is placed on the loop-type landing member. Subsequently, a rubber-coated steel roller of diameter of 3.25 in., a width of 1.75 in. and a weight of 4.5 lbs is rolled back and forth in the length direction of the tape tab 60 twice (a total of four passes).

The steel plate with the attached hook-type and loop-type materials is mounted horizontally into the lower jaw of an INSTRON test apparatus, Model 4201, which is set to have a cross-head speed of 12 in./minute, a Load Cell of 10.0 kg and a gage length of 2 in.

The leading edge of the tape tab 60 is placed in the upper jaw of the INSTRON apparatus .

The upper cross head is set in motion to pull the leading edge of the tape tab 60 off the loop-type landing member at an angle of 185° with respect to the loop-type landing member. When the maximum pull force has been reached, the crosshead is returned to the pre-set gage length.

The peak force, in grams, is recorded for at least four samples and is averaged.

Figure 3:
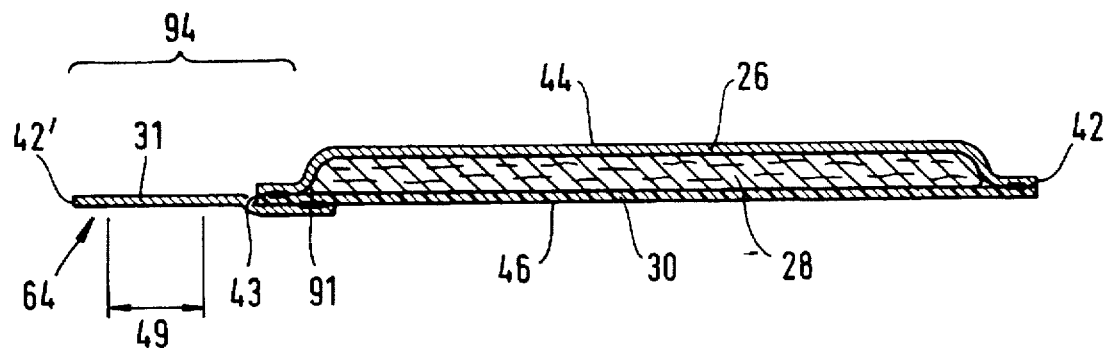
FIGS. 3–5 show cross-sectional views of different embodiments of absorbent articles having a first and second backsheet section along the longitudinal center line.
Figure 4:
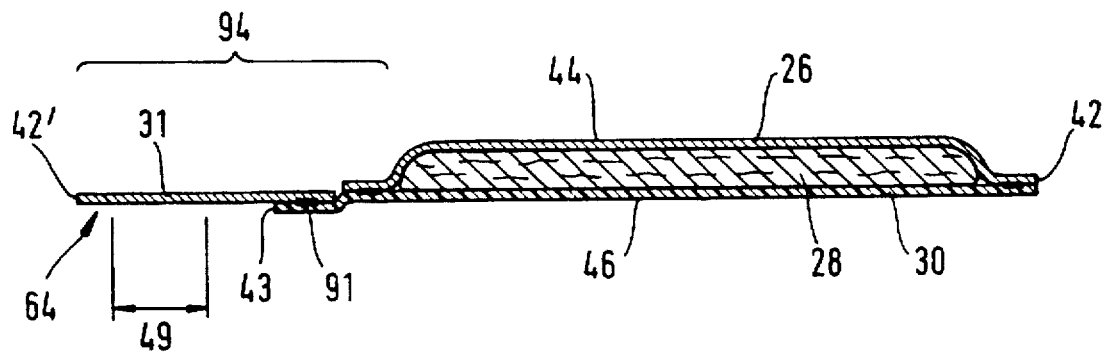

As shown in FIG. 3, the second section 31 of the backsheet forms a landing zone 49 in the front waist region 94. The second backsheet section 31 is attached along a line of attachment 91 on the garment-facing side 46 of the first backsheet section 30. The second section 31 forms a flexible waist panel which can conform to the movements of the wearer while maintaining a proper attachment to the hook-type fastening members 58. As shown in FIG. 4, the second section 31 may alternatively be connected to the user-facing side 44 of the first section 30. The second backsheet section 31 preferably is of a breathable material, such that ventilation of the skin below the second section can occur.

Figure 5:
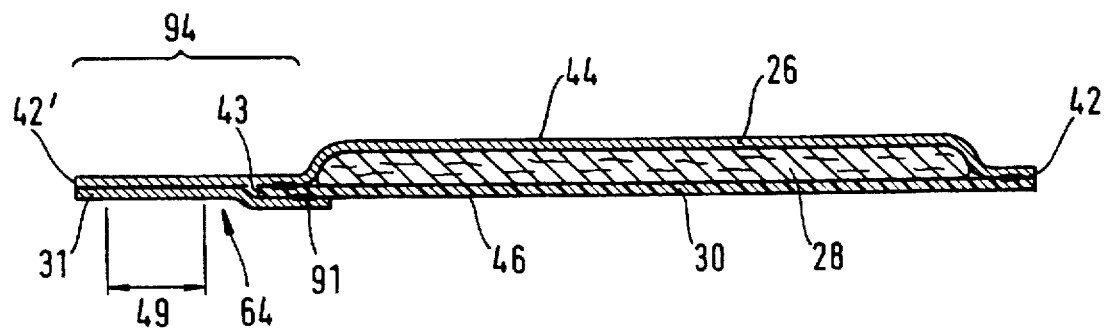

In FIG. 5, the second backsheet section 31 underlies the topsheet 26. Such a dual layer construction of backsheet and topsheet in the front waist region 94, improves the resistance of the front waist region against roll-over. This improved flexural resistance allows the dual layer front waist region to flex and bend in a direction perpendicular to the plane of the second backsheet section 31 and the topsheet 26 to conform to the movements of the belly of the wearer.

Figure 6:
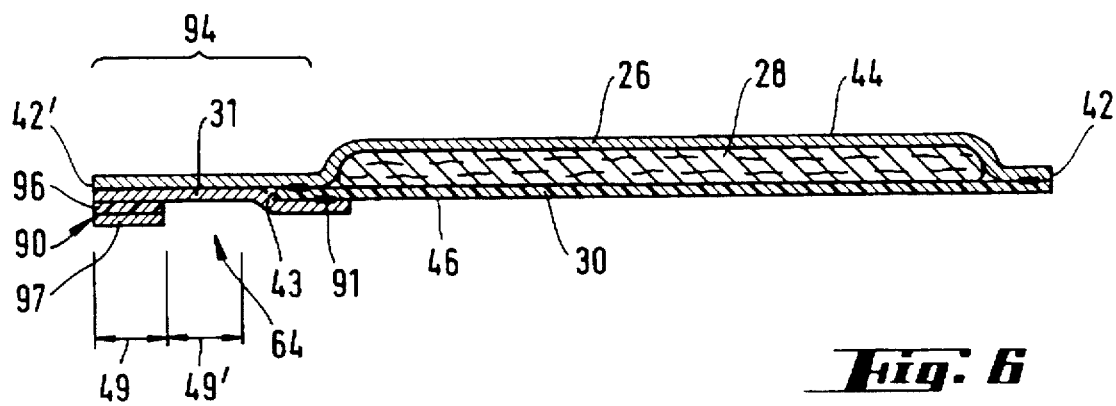
FIGS. 6 and 7 show cross-sectional views along the longitudinal centerline of an absorbent article comprising an elasticated front waist region.

As shown in FIG. 6, an elastic element 90 may be connected to the garmentfacing side 46 of the second backsheet section 31. The elastic element 90 may be an elastomeric film, the hook-type fastening members 58 being attachable to the part of the second section 31 which projects beyond the elastic film. In this case, the landing zone 49' is located outwardly from the elastic element 90. Alternatively, as is shown in FIG. 6, the elastic element 90 is a laminate of an elastic film 96 and a fibrous layer 97 to which the hook-type fasteners may engage. In this case the landing zone 49 is formed by the elastic element 90 such that the second backsheet section 31 may be comprised of a plastic film or of a fibrous material which in itself is unsuitable for attachment to the hook-type fastening members.

Figure 7:
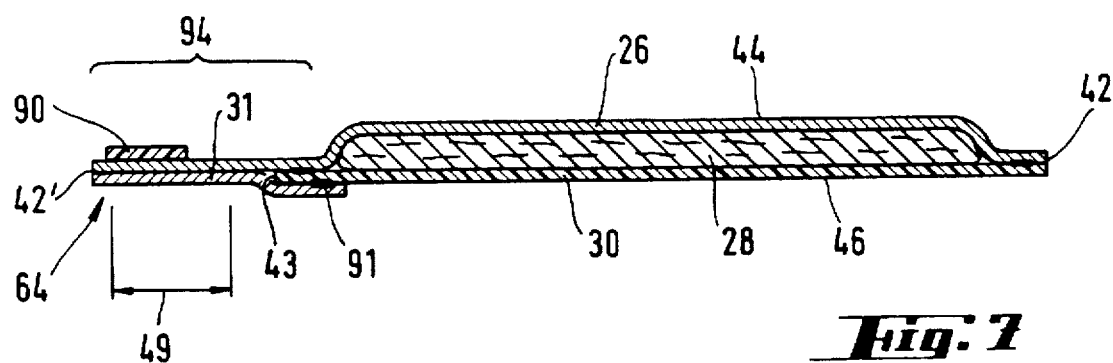
Figure 8:
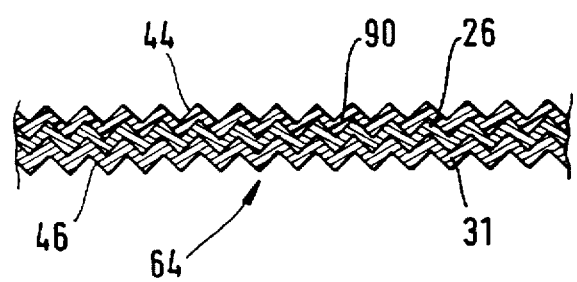
FIG. 8 shows a cross-sectional view of the front waist region of FIG. 7 along a line of cross-section perpendicular to the plane of the drawing of FIG. 7.

In FIG. 7, it is depicted that the elastic element 90 is located on the user-facing side 44 of the topsheet 26, on the user-facing side of the second backsheet section 31. FIG. 8 shows a cross-sectional view of the article according to FIG. 7, along a line of cross-section perpendicular to the plane of the drawing of FIG. 7 and extending through the elastic member 90. It can be seen that the garment-facing surface 46 of the second backsheet section 31 is contracted in gathers, which improve the fibers of the second backsheet section 31 to project outwardly and improve the fastening of the hook-type material thereto. Preferably the contractive force of the elastic element 90 is between 20 and 250 g for each 2.54 cm of width of the elastic element, upon extension of the element 90 by 2.54 cm. Most preferably the contractive force is about 150 g.

Figure 9:
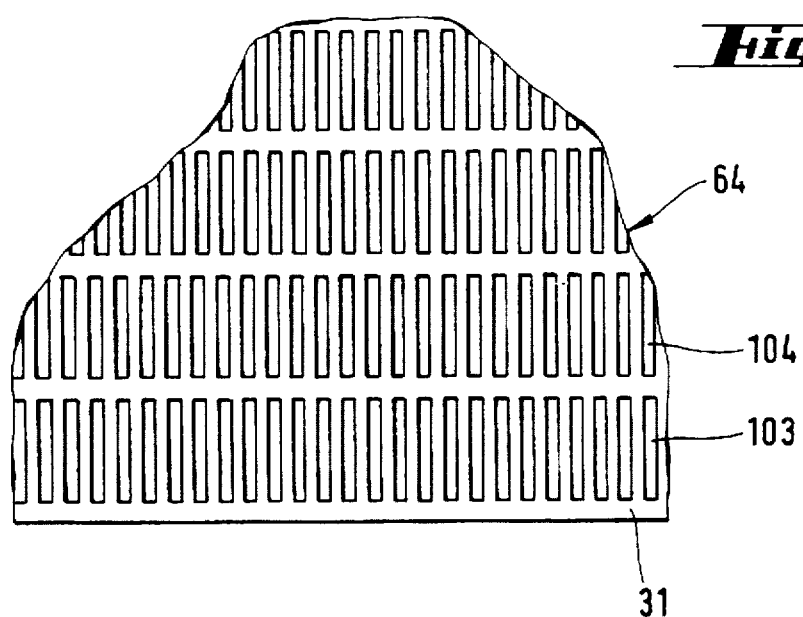
FIG. 9 shows a partial enlarged view of a landing member 64 comprising a number of parallel corrugations.

FIG. 9 shows a partial enlarged plan view of the garment-facing side of a second backsheet section 31, which comprises a number of parallel corrugations 103,104. These corrugations 103,104 may impart extensibility to the second section 31 and improve the surface texture of the second backsheet section for improved fastening of the hook-type material thereto. The process for imparting such surface structure has been described in detail in U.S. Pat. No. 5,196,000 and U.S. Pat. No. 5,236,430.

Figure 10:
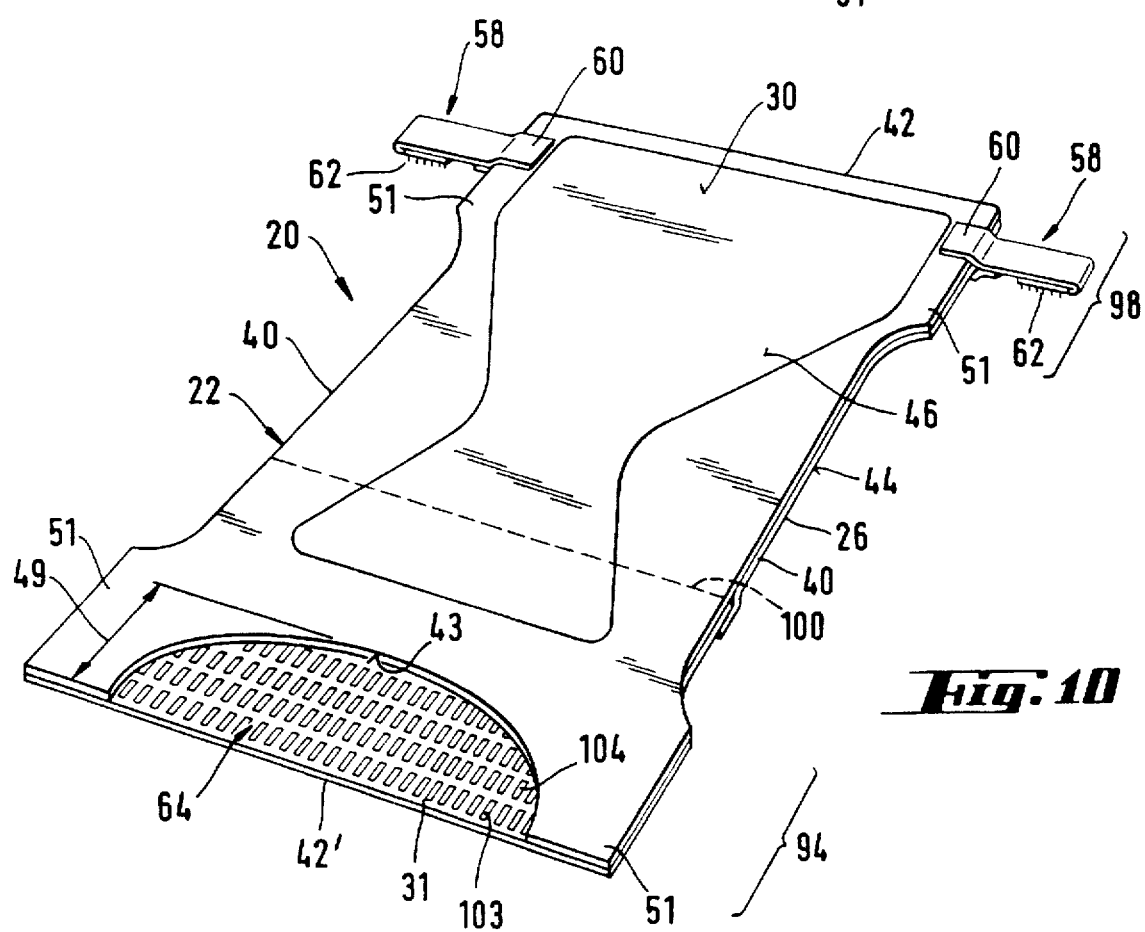
FIG. 10 shows a perspective view of an absorbent article comprising a landing zone having parallel corrugations as shown in FIG. 9.

In FIG. 10 it is shown that the front peripheral edge 43 of the first backsheet section 30 is curved such that the landing member 64 has an inwardly concave shape. The second backsheet section 31 forms the landing member 64 and comprises the parallel corrugations as shown in detail in FIG. 9. By providing the second backsheet section 31 with the parallel corrugations 103,104, the backsheet section 31 is especially adapted to expand and contract to conform to the movements of the wearer, in particular in the region of the belly. The second backsheet section 31 in FIG. 10 extends between the front transverse edge 42' and a back edge 100. The backsheet section 31 terminates at the back edge 100 and is connected across its surface to the first backsheet section 30, for instance by spiral patterns of adhesive. Alternatively, the back edge 100 of the second backsheet section may be located in the region of the back transverse edge 42.

I claim:

1. An absorbent article (20) comprising:
    a garment facing backsheet having two longitudinal sides (40),
    a front transverse edge (42'), a front waist region (94) located along the front transverse edge (42'), a back transverse edge (42), and a back waist region (98) located along the back transverse edge (42'), an absorbent core (28) joined to said backsheet; and
    a mechanical closing system (24) comprising:
        at least two hook-type fastening members (58) located in the back waist region (98) and extending transversely beyond each longitudinal side (40), and a landing zone (49,49') located in the front waist region (94) comprising a landing member (64) for mechanically engaging with the hook-type fastening members (58), wherein the backsheet comprises a first section (30), having a front peripheral edge (43) located outside the landing zone (49), and a second section (31) joined to the first section (30), the second section (31) extending longitudinally outwardly from the first section (30) toward the front transverse edge (42'), the second section being at least partly located in the front waist region (94) and forming the landing member (64), and wherein the second section (31) of the backsheet comprises an elastically extendible material, the elastically extendible material exerting a contractive force of between 20 and 250 g when the material is stretched by 2.54 cm.

2. Absorbent article according to claim 1, wherein the second section (31) comprises a laminate of a thermoplastic film (96) and a nonwoven material (97), the non-woven material (97) being located on the garment-facing side (46) of the backsheet.

3. Absorbent article according to claim 1, wherein the second section (31) of the backsheet is contracted by an elastic element (90) located in the front waist region (94).

4. Absorbent article (20) according to claim 1, wherein the first section (30) of the backsheet comprises a thermoplastic film or a combination of a thermoplastic film and a nonwoven material laminated to garment-facing side of the film, the second section (31) comprising a non-woven material.

5. Absorbent article (20) according to claim 1, wherein the second section (31) of the backsheet has been mechanically deformed in at least the landing zone (49) to modify the surface texture of the second section for improved mechanical engagement with the hook-type fasting members (58).

6. Absorbent article (20) according to any of claim 1, wherein the second section (30) of the backsheet has been mechanically deformed in at least the landing zone (49,49') to render the second section extensible at least in the direction of the front transverse edge (42').

7. Absorbent article (20) according to claim 1, wherein the second section (31) of the backsheet is attached to the the first section (30) of the backsheet along a front peripheral edge (43) of the first section 30 located outside the landing zone (49).

8. An absorbent article according to claim 1, wherein the elastically extendible material exerts a contractive force of between 120 and 170 g when the material is stretched by 2.54 cm.

* * * * *